United States Patent [19]
Cody et al.

[11] Patent Number: 6,136,798
[45] Date of Patent: Oct. 24, 2000

[54] COMPOUNDS INHIBITING THE ASSOCIATION OF THE PDGF RECEPTOR AND PHOSPHATIDYLINOSITOL 3-KINASE AND THEIR USE

[75] Inventors: Wayne Livingston Cody, Saline, Mich.; Annette Marian Doherty, Paris, France; Scott R. Eaton, Pinckney; Robert Lee Panek, Canton, both of Mich.

[73] Assignee: Warner-Lambert Company, Morris Plains, N.J.

[21] Appl. No.: 09/180,219

[22] PCT Filed: Apr. 21, 1997

[86] PCT No.: PCT/US97/06726

§ 371 Date: Feb. 22, 1999

§ 102(e) Date: Feb. 22, 1999

[87] PCT Pub. No.: WO97/43307

PCT Pub. Date: Nov. 20, 1997

Related U.S. Application Data

[60] Provisional application No. 60/018,373, May 16, 1996.

[51] Int. Cl.$^7$ .............................. A61K 31/662; C07F 9/40
[52] U.S. Cl. ........................... 514/141; 514/19; 514/616; 514/824; 514/825; 514/863; 530/330; 530/331; 558/170; 558/172; 558/173; 562/15
[58] Field of Search ............................... 564/153; 514/19, 514/616, 141, 824, 863, 825; 530/330, 331; 558/170, 172, 173; 562/15

[56] References Cited

U.S. PATENT DOCUMENTS

| | | |
|---|---|---|
| 5,382,569 | 1/1995 | Cody et al. . |
| 5,763,577 | 6/1998 | Bolton et al. ........................... 530/330 |

FOREIGN PATENT DOCUMENTS

| | | |
|---|---|---|
| 94/08600 | 4/1994 | WIPO . |
| 97/08193 | 3/1997 | WIPO . |
| 97/43307 | 11/1997 | WIPO . |

OTHER PUBLICATIONS

PCT International Search Report, mailing date: Oct. 7, 1997.
Ramalingam, K., et al., "Structure–Activity Studies of Phosphorylated Peptide Inhibitors of the Association of Phosphatidylinositol 3–Kinase with PDGF–β Receptor," *Bioorganic & Medicinal Chemistry*, 1995, vol. 3, No. 9, pp. 1263–1272.
Eaton, S. R., et al., "Structure–Activity Relationships of Peptides That Block the Association of PDGF–β Receptor with Phosphatidylinositol 3–Kinase," Peptides: Chemistry, Structure and Biology, Proceedings of the 14$^{th}$ American Peptide Symposium, eds. Kaumaya, P. T. P., and Hodges, R. S., 1996, Kinswinford: Mayflower Scientfic Ltd., pp. 414–415.
Ramalingam, K., et al., "Side reactions in the synthesis of phosphotyrosine–containing peptides," *Letters in Peptide Science*, 1994, vol. 1, pp. 73–79.
Domchek, S. M., et al., "Inhibition of SH2 Domain/Phosphoprotein Association by a Nonhydrolyzable Phosphonopeptide," *Biochemistry*, 1992, vol. 31, pp. 9865–9870.
Burke, Jr., T. R., et al., "Potent Inhibition of Insulin Receptor Dephosphorylation by a Hexamer Peptide Containing the Phosphotyrosyl Mimetic F$_2$Pmp," *Biochemical and Biophysical Research Communications*, Oct. 14, 1994, vol. 204, No. 1, pp. 129–134.
Burke, Jr., T. R., et al., "Nonhydrolyzable Phosphotyrosyl Mimetics for the Preparation of Phosphatase–Resistant SH2 Domain Inhibitors," *Biochemistry*, 1994, vol. 33, pp. 6490–6494.
Klippel, A., et al., "The C–Terminal SH2 Domain of p85 Accounts for the High Affinity and Specificity of the Binding of Phosphatidylinositol 3–Kinase to Phosphorylated Platelet–Derived Growth Factor β Receptor," *Molecular and Cellular Biology*, Apr., 1992, vol. 12, No. 4, pp. 1451–1459.
Burke, Jr., T. R., et al., "Cyclic Peptide Inhibitors of Phosphatidylinositol 3–Kinase p85 SH2 Domain Binding," *Biochemical and Biophysical Research Communications*, Jun. 30, 1994, vol. 201, No. 3, pp. 1148–1153.
Roller, P. P., et al., "Norleucine as a Replacement for Methionine in Phosphatase–Resistant Linear and Cyclic Peptides which Bind to P85 SH2 Domains," *Bioorg. Med. Chem Lett.*, 1994, vol. 4, No. 15, pp. 1879–1882.
Fantl, W. J., et al., "Distinct Phosphotyrosines on a Growth Factor Receptor Bind to Specific Molecules That Mediate Different Signaling Pathways," *Cell*, 1992, vol. 69, pp. 413–423.
Eaton, S. R., et al., "Proline Modifications of a Phosphotyrosine Pentapeptide from the PDGF β–Receptor," 24$^{th}$ National Medicinal Chemistry Symposium, Jun., 1994, poster presentation.
Ramalingam, K., et al., "Structure–Activity Studies of Peptide Inhibitors for the Binding of SH2 Domains of the p85 Subunit of Phosphatidylinositol 3–Kinase with the PDGF–β Receptor," 208$^{th}$ American Chemical Society National Meeting, Aug., 1994, poster presentation.
Eaton, S. R., et al., "Structure–Activity Relationships of Peptides that Block the Association of PDGF β–Receptor with Phosphatidylinositol 3–Kinase," 14$^{th}$ American Peptide Symposium, Jun., 1995, poster presentation.
Ramalingam, K., et al, "Use of Boc–Tyr[PO$_3$(Bzl)$_2$]–OH in the Synthesis of Methionine Containing Phosphopeptides," ACS Regional Meeting, Ann Arbor, Jun., 1994, poster presentation.

*Primary Examiner*—Shailendra Kumar
*Attorney, Agent, or Firm*—Charles W. Ashbrook

[57] ABSTRACT

The present invention provides compounds that inhibit the association of platelet-derived growth factor and phosphatidylinositol 3-kinase. The present invention also provides pharmaceutical compositions that contain a compound that inhibits the association of platelet-derived growth factor and phosphatidylinosital 3-kinase, and methods of treating cancer, restenosis, arthritis, dermatitis, atherosclerosis, vein graft intimal hyperplasia, neointimal hyperplasia of vascular smooth muscle and psoriasis using compounds that inhibit the association of platelet-derived growth factor and phosphatidylinositol 3-kinase.

16 Claims, No Drawings

COMPOUNDS INHIBITING THE ASSOCIATION OF THE PDGF RECEPTOR AND PHOSPHATIDYLINOSITOL 3-KINASE AND THEIR USE

This application is a continuation of provisional application Ser. No. 60/018,373, filed on May 16, 1996.

FIELD OF THE INVENTION

This invention relates to compounds that inhibit the association of the platelet-derived growth factor receptor and phosphatidylinositol 3-kinase. This invention also relates to pharmaceutical compositions that contain a compound that inhibits the association of the platelet-derived growth factor receptor and phosphatidylinositol 3-kinase, and to methods of treating cancer, restenosis, arthritis, dermatitis, atherosclerosis, vein graft intimal hyperplasia, neointimal hyperplasia of vascular smooth muscle, and psoriasis using compounds that inhibit the association of the platelet-derived growth factor receptor and phosphatidylinositol 3-kinase.

BACKGROUND OF THE INVENTION

Many disease states are characterized by the uncontrolled proliferation and differentiation of cells. These disease states encompass a variety of cell types and maladies such as cancer, atherosclerosis, restenosis, arthritis, dermatitis, vein graft intimal hyperplasia, neointimal hyperplasia of vascular smooth muscle and psoriasis. The compounds can also be used to delay aging of the skin. The proliferation, differentiation and survival of cells are regulated by numerous extracellular signaling polypeptide growth factors, which have been implicated in these disease states. Some of the better characterized growth factors include the following: epidermal growth factor (EGF), fibroblast growth factors (FGFs), and platelet-derived growth factor (PDGF).

The effects of many growth factors are known to be mediated by high affinity receptor tyrosine kinases. The binding of growth factors to extracellular receptors activates intracellular tyrosine kinases that catalyze the phosphorylation of several tyrosines on intracellular protein substrates or the receptor (autophosphorylation). These phosphorylated tyrosines create high affinity binding sites for many secondary cellular proteins involved in signal transduction such as phosphatidylinositol 3-kinase (PI 3-kinase), phospholipase C-γ (PLC-γ), and ras-GTPase-activating protein (GAP), among others. These molecules contain homologous regions known as src homology 2 (SH2) domains that were first identified in src family protein tyrosine kinases (PTKs). SH2 domains confer high affinity interactions with specific phosphorylated tyrosine residues of the growth factor receptors. Further downstream signaling results in cellular proliferation. Thus, the blockade of these signal transduction pathways can be used in the treatment of proliferative diseases.

In particular, the binding of PDGF to cell surface receptors induces receptor dimerization, followed by autophosphorylation at multiple tyrosine residues, which initiates cytoplasmic signaling via secondary cellular proteins containing SH2 domains. Currently, more than twenty cytosolic proteins likely to be involved in signaling have been shown to contain SH2 domains. Of these, PI 3-kinase is an important member that interacts with many activated PTKs and is involved in both normal and oncogenic signal transduction. The role of PI 3-kinase in PDGF-mediated cell proliferation has been investigated by measuring the levels of DNA synthesis in NMuMG cells expressing wild-type versus those expressing mutant PDGF receptors. A significant increase in DNA synthesis was observed in cells expressing PDGF receptors that were specifically associated with PI 3-kinase. The important involvement of PI 3-kinase in cell motility was recently demonstrated by Wennstrom et al., *Oncogene*, 1994;9:651–60, who showed that in porcine aortic endothelial cells expressing the PDGF-β receptor, membrane ruffling and chemotaxis transduced by the PDGF-β receptor required PI 3-kinase binding.

PI 3-kinase is a heterodimeric enzyme and contains an 85 kDa (p85) noncatalytic subunit and a 110 kDa (p110) catalytic subunit. The p85 subunit has one src homology 3 (SH3) and two SH2 domains which bind to specific phosphorylated tyrosines on activated growth factor receptors. PI 3-kinase has been shown to interact specifically with the phosphorylated tyrosine 740 and tyrosine 751 residues of the PDGF-β receptor.

Of the two SH2 domains (N- and C-terminal) of the p85 subunit of PI 3-kinase, the C-terminal SH2 domain like the full-length p85 distinguishes between the wild-type and a mutant PDGF receptor lacking the PI 3-kinase binding site. Thus, the C-terminal SH2 domain of the p85 subunit (p85 C-SH2) accounts for the high affinity and specificity of the binding of PI 3-kinase to the PDGF-β receptor.

SUMMARY OF THE INVENTION

The present invention provides compounds having the Formula I

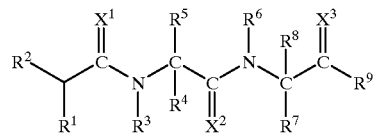

wherein
$X^1$, $X^2$, and $X^3$ are independently O or S;

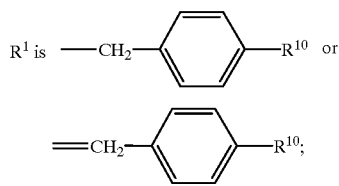

$R^2$ is hydrogen, $C_1$–$C_6$ alkyl, $C_2$–$C_6$ alkenyl, $C_2$–$C_6$ alkynyl, $C_3$–$C_7$ cycloalkyl, aryl, heteroaryl, —$NR^aR^b$, —$OR^c$, —$CO_2R^d$, —$NR^eCOR^f$, —$NR^gCO_2R^h$, —$COR^i$, —$NR^jCO_2$-fluorenylmethyl, —$NR^kCO_2CH_2$-phenyl, or —$NR^kCONHR^a$;

$R^3$ and $R^6$ are independently hydrogen or methyl;

$R^5$ is hydrogen, $C_1$–$C_8$ alkyl, —$(CH_2)_nCO_2H$, —$(CH_2)_nCO_2R^{11}$, or —$(CH_2)_nCONR^{12}R^{13}$;

$R^8$ is hydrogen, $C_1$–$C_8$ alkyl, $C_3$–$C_8$ cycloalkyl, or $R^6$ and $R^8$ together form a 3 to 8 membered ring;

$R^4$ and $R^7$ are independently hydrogen or methyl;

$R^9$ is —$NR^{14}R^{15}$, —$OR^{16}$, or —$SR^{17}$;

$R^{10}$ is —$CY^1Y^2PO_3R^{18}R^{19}$ or —$OPO_3R^{20}R^{21}$;

$R^a$, $R^b$, $R^c$, $R^d$, $R^e$, $R^g$, $R^j$, $R^k$, $R^{11}$, $R^{12}$, $R^{13}$, $R^{18}$, $R^{19}$, $R^{20}$, and $R^{21}$ are independently hydrogen or $C_1$–$C_6$ alkyl;

$R^h$, $R^i$, and $R^f$ are $C_1$–$C_6$ alkyl;

$R^{14}$, $R^{15}$, $R^{16}$, and $R^{17}$ are independently hydrogen, $C_1$–$C_8$ alkyl, $C_2$–$C_5$ alkenyl, $C_2$–$C_5$ alkynyl, $C_3$–$C_7$ cycloalkyl, or when $R^9$ is —$NR^{14}R^{15}$, $R^{14}$ and $R^{15}$ together with the nitrogen atom of —$NR^{14}R^{15}$ can form a ring having from 3 to 8 atoms;

$Y_1$ and $Y_2$ are independently hydrogen or halogen; and n is 1–4, and the pharmaceutically acceptable salts, esters, amides, and prodrugs thereof.

In a preferred embodiment of Formula I, $R^2$ is —$NR^eCOR^f$.

In a more preferred embodiment of Formula I, $R^2$ is —$NHCOCH_3$.

In another preferred embodiment of Formula I, $R^{10}$ is —$CF_2PO_3H_2$ or —$OPO_3H_2$.

In another preferred embodiment of Formula I, $R^9$ is —$NR^{14}R^{15}$.

In another preferred embodiment of Formula I, $R^1$ is

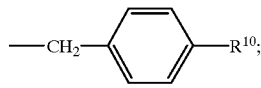

In a most preferred embodiment of Formula I, $R^1$ is

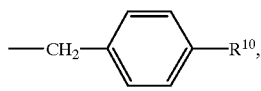

$R^2$ is —$NR^eCOR^f$, $R^{10}$ is —$CF_2PO_3H_2$ or —$OPO_3H_2$, and $R^9$ is —$NR^{14}R^{15}$.

In another embodiment, the invention provides compounds having the Formula II

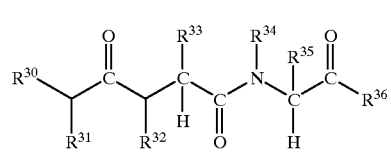

$R^{30}$ is hydrogen, —$NR^aR^b$, —$NR^eCOR^f$, —$NR^kCO_2CH_2$-phenyl, or —$NR^jCO_2$fluorenylmethyl;

$R^{31}$ is

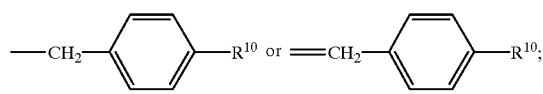

$R^{32}$ and $R^{34}$ are independently hydrogen or methyl;

$R^{33}$ is $C_1$–$C_8$ alkyl, —$(CH_2)_nCO_2H$, —$(CH_2)_nCO_2R^{11}$, or —$(CH_2)_nCONR^{12}R^{13}$;

$R^{35}$ is $C_1$–$C_8$ alkyl or $R^{35}$ and $R^{34}$ together form a 3 to 8 membered ring;

$R^{36}$ is —$NR^{14}R^{15}$;

$R^f$ is $C_1$–$C_6$ alkyl;

$R^{10}$ is —$CY^1Y^2PO_3R^{18}R^{19}$ or —$OPO_3R^{20}R^{21}$;

$R^a$, $R^b$, $R^e$, $R^j$, $R^k$, $R^{11}$, $R^{12}$, $R^{13}$, $R^{18}$, $R^{19}$, $R^{20}$, and $R^{21}$ are independently hydrogen or $C_1$–$C_6$ alkyl;

$R^{14}$ and $R^{15}$ are independently hydrogen, $C_1$–$C_8$ alkyl, $C_2$–$C_5$ alkenyl, $C_2$–$C_5$ alkynyl, $C_3$–$C_7$ cycloalkyl, or when $R^{36}$ is —$NR^{14}R^{15}$, $R^{14}$ and $R^{15}$ together with the nitrogen atom of —$NR^{14}R^{15}$ can form a ring having from 3 to 8 atoms;

n is 1–2; and $Y^1$ and $Y^2$ are independently hydrogen or halogen, and the pharmaceutically acceptable salts, esters, amides, and prodrugs thereof.

In another embodiment, the invention provides compounds of the Formula III

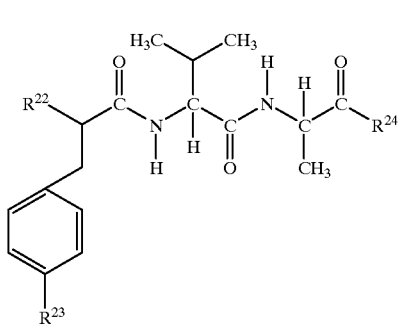

wherein $R^{22}$ is hydrogen, —$NR^aR^b$, —$NR^eCOR^f$, $NR^kCO_2CH_2$-phenyl, or —$NR^jCO_2$fluorenylmethyl;

$R^{23}$ is —$CY^1Y^2PO_3R^{18}R^{19}$ or —$OPO_3R^{20}R^{21}$;

$R^{24}$ is —$NR^{14}R^{15}$;

$R^a$, $R^b$, $R^e$, $R^j$, $R^k$, $R^{18}$, $R^{19}$, $R^{20}$, and $R^{21}$ are independently hydrogen or $C_1$–$C_6$ alkyl;

$R^f$ is $C_1$–$C_6$ alkyl;

$R^{14}$ and $R^{15}$ are independently hydrogen, $C_1$–$C_8$ alkyl, $C_2$–$C_5$ alkenyl, $C_2$–$C_5$ alkynyl, or $C_3$–$C_7$ cycloalkyl; and $Y^1$ and $Y^2$ are independently hydrogen or halogen, and the pharmaceutically acceptable salts, esters, amides, and prodrugs thereof.

In a preferred embodiment of Formula III, $R^{22}$ is —$NR^eCOR^f$.

In more preferred embodiment of Formula III, $R^{22}$ is —$NHCOCH_3$.

In another preferred embodiment of Formula III, $R^{23}$ is —$CF_2PO_3H_2$ or —$OPO_3H_2$.

In another preferred embodiment of Formula III, $R^{24}$ is —$NR^{14}R^{15}$.

In a most preferred embodiment of Formula III, $R^{22}$ is —$NR^eCOR^f$, $R^{23}$ is —$CF_2PO_3H_2$ or —$OPO_3H_2$, and $R^{24}$ is —$NR^{14}R^{15}$.

The present invention also provides a method of treating cancer that comprises administering to a patient having cancer a therapeutically effective amount of a compound of Formula I, II, or III.

The present invention also provides a method of treating or preventing restenosis that comprises administering to a patient having restenosis or at risk of having restenosis a therapeutically effective amount of a compound of Formula I, II, or III.

The present invention also provides a method of treating arthritis that comprises administering to a patient having arthritis a therapeutically effective amount of a compound of Formula I, II, or III.

The present invention also provides a method of treating dermatitis that comprises administering to a patient having dermatitis a therapeutically effective amount of a compound of Formula I, II, or III.

The present invention also provides a method of treating atherosclerosis that comprises administering to a patient having atherosclerosis a therapeutically effective amount of a compound of Formula I, II, or III.

The present invention also provides a method of treating vein graft intimal hyperplasia that comprises administering to a patient having vein graft intimal hyperplasia a therapeutically effective amount of a compound of Formula I, II, or III.

The present invention also provides a method of treating neointimal hyperplasia of vascular smooth muscle that comprises administering to a patient having neointimal hyperplasia of vascular smooth muscle a therapeutically effective amount of a compound of Formula I, II, or III.

The present invention also provides a method of treating psoriasis that comprises administering to a patient having psoriasis a therapeutically effective amount of a compound of Formula I, II, or III.

The present invention also provides a pharmaceutically acceptable composition that comprises a compound of Formula I, II, or III.

The present invention also provides the compounds

[1S-[1R*[R*(R*)]]]-2-[2-(2-Acetylamino-3-{4-[(diethoxy-phosphoryl)-difluoro-methyl]-phenyl}-propionylamino)-3-methyl-butyrylamino]-propionic acid;

[1S-[1R*[R*(R*)]]]-[(4-{2-Acetylamino-2-[1-(1-dihexylcarbamoyl-ethylcarbamoyl)-2-methyl-propyl-carbamoyl]-ethyl}-phenyl)-difluoro-methyl]-phosphonic acid diethyl ester;

[1S-[1R*[R*(R*)]]]-[(4-{2-Acetylamino-2-[1-(1-dihexylcarbamoyl-ethylcarbamoyl)- 2-methyl-propyl-carbamoyl]-ethyl}-phenyl)-difluoro-methyl]-phosphonic acid;

[1S-[1R*[R*(R*)]]]-[(4-{2-Acetylamino-2-[1-(1-dipentylcarbamoyl-ethylcarbamoyl)-2-methyl-propylcarbamoyl]-ethyl}-phenyl)-difluoro-methyl]-phosphonic acid;

[1S-[1R*[R*(R*)]]]-[(4-{2-Acetylamino-2-[1-(1-dipentylcarbamoyl-ethylcarbamoyl)-2-methyl-propylcarbamoyl]-ethyl}-phenyl)-difluoro-methyl]-phosphonic acid;

[1S-[1R*[R*(R*)]]]-[(4-{2-Acetylamino-2-[1-(1-dioctylcarbamoyl-ethylcarbamoyl)-2-methyl-propylcarbamoyl]-ethyl}-phenyl)-difluoro-methyl]-phosphonic acid;

[1S-[1R*[R*(R*)]]]-Phosphoric acid mono-(4-{2-acetylamino-2-[1-(1-dibutylcarbamoyl-ethylcarbamoyl)-2-methyl-propylcarbamoyl]-ethyl}-phenyl) ester;

[1R-[1R*[S*(S*)]]]-Phosphoric acid mono-(4-{2-acetylamino-2-[1-(1-dibutylcarbamoyl-ethylcarbamoyl)-2-methyl-propylcarbamoyl]-ethyl}-phenyl) ester;

[1S-[1R*[R*(R*)]]]-Phosphoric acid mono-(4-{2-acetylamino-2-[1-(1-dipentylcarbamoyl-ethylcarbamoyl)-2-methyl-propylcarbamoyl]-ethyl}-phenyl) ester;

[1R-[1R*[S*(S*)]]]-Phosphoric acid mono-(4-{2-acetylamino-2-[1-(1-dipentylcarbamoyl-ethylcarbamoyl)-2-methyl-propylcarbamoyl]-ethyl}-phenyl) ester;

[1S-[1R*[R*(R*)]]]-Phosphoric acid mono-(4-{2-acetylamino-2-[1-(1-dihexylcarbamoyl-ethylcarbamoyl)-2-methyl-propylcarbamoyl]-ethyl}-phenyl) ester;

[S-[R*[R*(S*)]]]-Phosphoric acid mono-(4-{2-acetylamino-2-[1-(1-dihexylcarbamoyl-ethylcarbamoyl)-2-methyl-propylcarbamoyl]-ethyl}-phenyl) ester;

[S-[R*[R*(S*)]]]-Phosphoric acid mono-(4-{2-acetylamino-2-[1-(1-dioctylcarbamoyl-ethylcarbamoyl)-2-methyl-propylcarbamoyl]-ethyl}-phenyl) ester;

[1S-[1R*[R*(R*)]]]-2-{2-[2-Acetylamino-3-(4-benzyloxy-phenyl)-propionylamino]-3-methyl-butyrylamino}-propionic acid;

[1S-[1R*[R*(R*)]]]-2-[2-Acetylamino-3-(4-benzyloxy-phenyl)-propionylamino]-N-(1-dihexylcarbamoyl-ethyl)-3-methyl-butyramide;

[1S-[1R*[R*(R*)]]]-Phosphoric acid mono-(4-{2-acetylamino-2-[1-(1-dihexylcarbamoyl-ethylcarbamoyl)-2-methyl-propylcarbamoyl]-ethyl}-phenyl) ester;

[S-(R*,R*)]-2-{2-[3-(4-Benzyloxy-phenyl)-propionylamino]-3-methyl-butyrylamino}-propionic acid;

[S-(R*,R*)]-2-[3-(4-Benzyloxy-phenyl)-propionylamino]-N-(1-dihexylcarbamoyl-ethyl)-3-methyl-butylamide; and

[S-(R*,R*)]-Phosphoric acid mono-(4-({2-[1-(1-dihexylcarbamoyl-ethylcarbamoyl)-2-methyl-propylcarbamoyl]-ethyl}-phenyl) ester.

DETAILED DESCRIPTION OF THE INVENTION

The present invention provides compounds having the Formula I

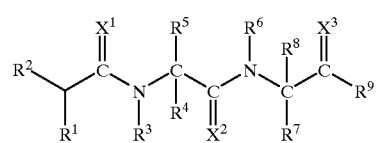

wherein $X^1$, $X^2$, and $X^3$ are independently O or S;

$R^1$ is

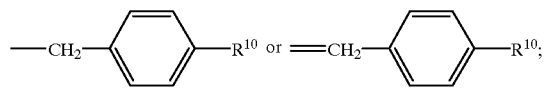

$R^2$ is hydrogen, $C_1$–$C_6$ alkyl, $C_2$–$C_6$ alkenyl, $C_2$–$C_6$ alkynyl, $C_3$–$C_7$ cycloalkyl, aryl, heteroaryl, —$NR^aR^b$, —$OR^c$, —$CO_2R^d$, —$NR^eCOR^f$, —$NR^gCOR^h$, —$COR^i$, —$NR^jCO_2$-fluorenylmethyl, —$NR^kCO_2CH_2$-phenyl, or —$NR^kCONHR^a$;

$R^3$ and $R^6$ are independently hydrogen or methyl;

$R^5$ and is hydrogen, $C_1$–$C_8$ alkyl, —$(CH_2)_nCO_2H$, —$(CH_2)_nCO_2R^{11}$, or —$(CH_2)_nCONR^{12}R^{13}$;

$R^8$ is hydrogen, $C_1$–$C_8$ alkyl, $C_3$–$C_8$ cycloalkyl, or $R^6$ and $R^8$ together form a 3 to 8 membered ring;

$R^4$ and $R^7$ are independently hydrogen or methyl;

$R^9$ is —$NR^{14}R^{15}$, —$OR^{16}$ or —$SR^{17}$;

$R^{10}$ is —$CY^1Y^2PO_3R^{18}R^{19}$ or —$OPO_3R^{21}$;

$R^a$, $R^b$, $R^c$, $R^d$, $R^e$, $R^g$, $R^j$, $R^k$, $R^{11}$, $R^{12}$, $R^{13}$, $R^{18}$, $R^{19}$, $R^{20}$, and $R^{21}$ are independently hydrogen or $C_1$–$C_6$ alkyl;

$R^h$, $R^i$, and $R^f$ are $C_1$–$C_6$ alkyl;

$R^{14}$, $R^{15}$, $R^{16}$, and $R^{17}$ are independently hydrogen, $C_1$–$C_8$ alkyl, $C_2$–$C_5$ alkenyl, $C_2$–$C_5$ alkynyl, $C_3$–$C_7$ cycloalkyl, or when R$^9$ is —NR$^{14}$R$^{15}$, R$^{14}$ and R$^{15}$ together with the nitrogen atom of —NR$^{14}$R$^{15}$ can form a ring having from 3 to 8 atoms;

Y$^1$ and Y$^2$ are independently hydrogen or halogen; and n is 1–4, and the pharmaceutically acceptable salts, esters, amides, and prodrugs thereof.

In a preferred embodiment, the present invention provides compounds having the Formula II

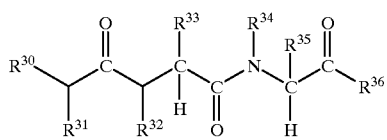

II

R$^{30}$ is hydrogen, —NR$^a$R$^b$, —NR$^e$COR$^f$, —NR$^k$CO$_2$CH$_2$-phenyl, or —NR$^j$CO$_2$fluorenylmethyl;

R$^{31}$ is

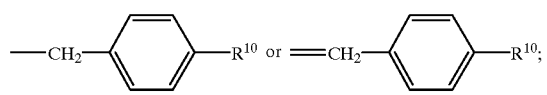

R$^{32}$ and R$^{34}$ are independently hydrogen or methyl;

R$^{33}$ is C$_1$–C$_8$ alkyl, —(CH$_2$)$_n$CO$_2$H, —(CH$_2$)$_n$CO$_2$R$^{11}$, or —(CH$_2$)$_n$CONR$^{12}$R$^{13}$;

R$^{35}$ is C$_1$–C$_8$ alkyl or R$^{35}$ and R$^{34}$ together form a 3 to 8 membered ring;

R$^{36}$ is —NR$^{14}$R$^{15}$;

R$^f$ is C$_1$–C$_6$ alkyl;

R$^{10}$ is —CY$^1$Y$^2$PO$_3$R$^{18}$R$^{19}$ or —OPO$_3$R$^{20}$R$^{21}$;

R$^a$, R$^b$, R$^e$, R$^j$, R$^k$, R$^{11}$, R$^{12}$, R$^{13}$, R$^{18}$, R$^{19}$, R$^{20}$, and R$^{21}$ are independently hydrogen or C$_1$–C$_6$ alkyl;

R$^{14}$ and R$^{15}$ are independently hydrogen, C$_1$–C$_8$ alkyl, C$_2$–C$_5$ alkenyl, C$_2$–C$_5$ alkynyl, C$_3$–C$_5$ cycloalkyl, or when R$^{36}$ is —NR$^{14}$R$^{15}$, R$^{14}$ and R$^{15}$ together with the nitrogen atom of —NR$^{14}$R$^{15}$ can form a ring having from 3 to 8 atoms;

n is 1–2; and

Y$^1$ and Y$^2$ are independently hydrogen or halogen, and the pharmaceutically acceptable salts, esters, amides, and prodrugs thereof.

In another embodiment, the invention provides compounds of the Formula III

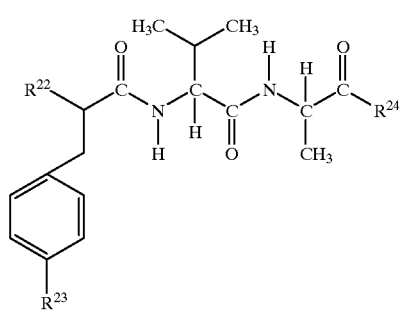

III wherein

R$^{22}$ is hydrogen, —NR$^a$R$^b$, —NR$^e$COR$^f$, —NR$^k$CO$_2$CH$_2$-phenyl, or —NR$^j$CO$_2$-fluorenylmethyl;

R$^{23}$ is —CY$^1$Y$^2$PO$_3$R$^{18}$R$^{19}$ or —OPO$_3$R$^{20}$R$^{21}$;

R$^{24}$ is —NR$^{14}$R$^{15}$;

R$^a$, R$^b$, R$^e$, R$^j$, R$^k$, R$^{18}$, R$^{19}$, R$^{20}$, and R$^{21}$ are independently hydrogen or C$_1$–C$_6$ alkyl;

R$^f$ is C$_1$–C$_6$ alkyl;

R$^{14}$, R$^{15}$, R$^{16}$, and R$^{17}$ are independently hydrogen, C$_1$–C$_8$ alkyl, C$_2$–C$_5$ alkenyl, C$_2$–C$_5$ alkynyl, or C$_3$–C$_7$ cycloalkyl; and Y$^1$ and Y$^2$ are independently hydrogen or halogen, and the pharmaceutically acceptable salts, esters, amides, and prodrugs thereof.

The term "alkyl" means a straight or branched chain hydrocarbon. Representative examples of alkyl groups are methyl, ethyl, propyl, isopropyl, isobutyl, butyl, tert-butyl, sec-butyl, pentyl and hexyl.

The term "halogen" includes chlorine, fluorine, bromine and iodine.

The term "alkenyl" means a branched or straight chain hydrocarbon having one or more carbon—carbon double bond.

The term "aryl" means an aromatic hydrocarbon. Representative examples of aryl groups include phenyl and naphthyl.

The term "heteroatom" includes oxygen, nitrogen and sulfur.

The term "heteroaryl" means an aryl group wherein one or more carbon atom of the aromatic hydrocarbon has been replaced with a heteroatom.

The term "cycloalkyl" means a cyclic hydrocarbon. Examples of cycloalkyl groups include cyclopropyl, cyclobutyl, cyclopentyl, and cyclohexyl.

The compounds of Formula I, II, or III can be used to treat patients having cancer or restenosis. The compounds of Formula I, II, or III can also be used to prevent restenosis in patients who are at risk of having restenosis. In addition, the compounds of Formula I, II, or III can be used to treat vein graft intimal hyperplasia, atherosclerosis, neointimal hyperplasia of vascular smooth muscle and psoriasis. The compounds can also be used to delay aging of the skin. Those skilled in the art are readily able to identify patients having cancer or restenosis or those who are at risk if having restenosis. For example, patients undergoing balloon angioplasty, graft or shunt therapy are at risk of developing restenosis. Cancer and restenosis can be treated by the compounds of Formula I, II, or III by administering to a patient having cancer or restenosis or at risk of having restenosis a therapeutically effective amount of a compounds of Formula I, II, or III. The term "patient" include animals such as dogs, cats, cows, as well as humans. A therapeutically effective amount can be determined by those skilled in the art by administering a compound of Formula I, II, or III and observing the symptoms of the disease. A therapeutically effective amount of a compound of Formula I, II, or III is an amount of compound that ameliorates a symptom of the disease.

The compounds of Formula I, II, or III can be administered by itself or as part of a pharmaceutically acceptable composition. Such pharmaceutically acceptable compositions are well-known to those skilled in the art.

The compositions can be administered to humans and animals either orally, rectally, parenterally (intravenously, intramuscularly, or subcutaneously), intracisternally, intravaginally, intraperitoneally, intravesically, locally (powders, ointments or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Solid dosage forms for oral administration include capsules, tablets, pills, powders and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alignates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example paraffin, (f) absorption accelerators, as for. example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, degrees, capsules, pills, and granules can be prepared with coatings and shells, such as enteric coatings and others well-known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, as, for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, and sesame oil, glycerol, tetrahydrofurfuryl alcohol, polyethyleneglycols, and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar—agar, and tragacanth, or mixtures of these substances, and the like.

Compositions for rectal administrations are preferably suppositories which can be prepared by mixing the compounds of the present invention with suitable nonirritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers or propellants as may be required. Ophthalmic formulations, eye ointments, powders, and solutions are also contemplated as being within the scope of this invention.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgement, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively nontoxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactiobionate and laurylsulphonate salts, and the like. These may include cations based on the alkali and alkaline earth metals, such as sodium, lithium, potassium, calcium, magnesium, and the like, as well as nontoxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, S. M. Berge, et al., "Pharmaceutical Salts," *J. Pharm. Sci.*, 1977;66:1–19 which is incorporated herein by reference).

Examples of pharmaceutically acceptable, nontoxic esters of the compounds of this invention include $C_1$–$C_6$ alkyl esters wherein the alkyl group is a straight or branched chain. Acceptable esters also include $C_5$–$C_7$ cycloalkyl esters as well as arylalkyl esters such as, but not limited to benzyl. $C_1$–$C_4$ alkyl esters are preferred. Esters of the compounds of the present invention may be prepared according to conventional methods.

Examples of pharmaceutically acceptable, nontoxic amides of the compounds of this invention include amides derived from ammonia, primary $C_1$–$C_6$ alkyl amines and secondary $C_1$–$C_6$ dialkyl amines wherein the alkyl groups are straight or branched chain. In the case of secondary amines the amine may also be in the form of a 5- or 6-membered heterocycle containing one nitrogen atom. Amides derived from ammonia, $C_1$–$C_3$ alkyl primary amines and $C_1$–$C_2$ dialkyl secondary amines are preferred. Amides of the compounds of the invention may be prepared according to conventional methods.

The term "prodrug" refers to compounds that are rapidly transformed in vivo to yield the parent compound of the above formulas, for example, by hydrolysis in blood. A thorough discussion is provided in T. Higuchi and V. Stella, "Pro-drugs as Novel Delivery Systems," Vol 14 of the A.C.S. Symposium Series, and in *Bioreversible Carriers in Drug Design*, ed. Edward B. Roche, American Pharmaceutical Association and Pergamon Press, 1987, both of which are incorporated herein by reference.

The compounds of the present invention can be administered to a patient at dosage levels in the range of about 0.1 to about 1,000 mg per day. For a normal human adult having a body weight of about 70 kg, a dosage in the range of about 0.01 to about 100 mg per kilogram of body weight per day is preferred. The specific dosage used, however, can vary. For example, the dosage can depended on a number of factors including the requirements of the patient, the severity of the condition being treated, and the pharmacological activity of the compound being used. The determination of optimum dosages for a particular patient is well known to those skilled in the art.

The compounds of the present invention can exist in different stereoisomeric forms by virtue of the presence of asymmetric centers in the compounds. It is contemplated that all stereoisomeric forms of the compounds as well as mixture thereof, including racemic mixtures, form part of this invention. Moreover, if a portion of the compounds of the present invention represents an amino acid, preferable the amino acid has the L configuration.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The examples presented below are intended to illustrate particular embodiments of the invention and are not intended to limit the scope of the specification, including the claims, in any manner.

EXAMPLES

Some abbreviations used in this application are presented in tabular form below other are defined where they occur in the specification.
Ac=acetyl
$CF_2Pmp$=4-phosphono(difluoromethyl)phenylalanine
OEt=O-ethyl ester
Val=valine
Ala=alanine
Fmoc=9-fluorenylmethoxycarbonyl
TFA=trifluoroacetic acid
EGF=epidermal growth factor
FGF=fibroblast growth factor
PDGF=platelet derived growth factor
DCC=N,N-dicyclohexylcarbodiimide
HOBt=N-hydroxybenzotriazole
DMAP=4-dimethylaminopyridine
NMP=N-methylpyrrolidinone HPLC=high pressure liquid chromatography
RP-HPLC=reverse phase high pressure liquid chromatography
$Ac_2O$=acetic anhydride
HOAc=acetic acid
HATU=O-(7-azabenzotriazol-1-yl)-1,1,3,3-tetramethyl-uroniuimhexafluorophosphate
HOAt=1-hydroxy-7-azabenzotriazole
DIEA=N,N-diisopropylethylamine
TMSOTf=trimethylsilyl trifluoromethanesulfonate
DMS=dimethyl sulfide
EDT=1,2-ethanedithiol
DMF=N,N-dimethylformamide
Boc=t-butyloxycarbonyl
DCM=dichloromethane
THF=tetrahydrofuran
Ppa=3-[4-(benzyl ether)-phenyl]propionic acid
Bzl=benzyl
PMSF=phenylmethylsulfonylfluoride
RASMC=rat aortic smooth muscle cells
SMC=smooth muscle cells
DMSO=dimethylsulfoxide
EDTA=ethylenediaminetetraacetic acid
EGTA=ethylene glycol-bis(β-aminoethyl ether)-N, N, N', N'-tetraacetic acid
TLC=thin layer chromatography The compounds of the present invention can be synthesized in accordance with the following general scheme:

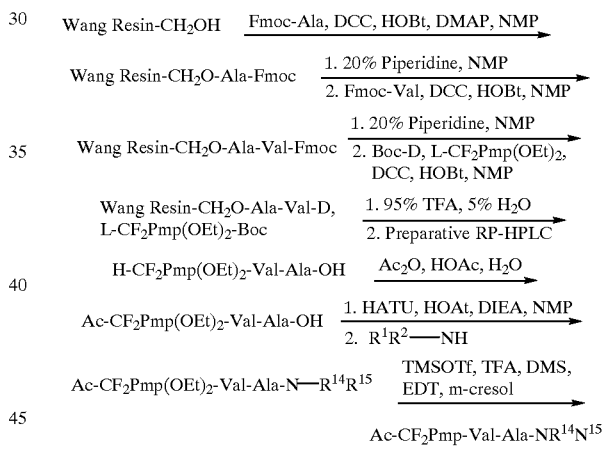

Example 1

Step A: Preparation of [1S-[1R*[R*(R*)]]]-2-[2-(2-Acetylamino-3-{4-[(diethoxy-phosphoryl)-difluoro-methyl]-phenyl}-propionylamino)-3-methyl-butyrylamino]-propionic acid [Ac-$CF_2Pmp(OEt)_2$-Val-Ala-OH]

Starting with 4.44 g of Fmoc-Ala-Wang-resin, which may be obtained from Advanced Chemtech, Louisville, Ky.), 0.45 meq of Fmoc-Ala per gram of resin, 2.00 mmol total), the resin was washed with N,N-dimethylformamide (DMF, 3x) N-methylpyrrolidinone (NMP, 3x) and the Fmoc protecting group was removed by two treatments with 20% piperidine in NMP. To the resulting free amine was coupled Fmoc-Val-OH (2.712 g, 4.0 eq.) in the presence of N,N-dicyclohexyl-carbodiimide (DCC, 1.652 g, 4.0 eq.) and N-hydroxy-benzotriazole (HOBt, 1.08 g, 4.0 eq.) in NMP. After the reaction was complete, as judged by the Kaiser ninhydrin test, for example, Kaiser, et al. *Anal. Biochem.*, 1970;34:595–8), the resin was washed with NMP (3x) and the Fmoc amino protecting group was removed, as above. To the resulting free amine was coupled Boc-D,L-CF$_2$Pmp (OEt)$_2$ (1.852 g, 2.0 eq.) in the presence of DCC (0.824 g, 2.0 eq.) and HOBt (0.54 g, 2.0 eq.) in NMP. After the reaction was complete, as judged by the ninhydrin test, the resin was washed with NMP (3×), dichloromethane (DCM, 3×) and dried under reduced pressure (4.77 g) to yield Boc-D,L-CF$_2$Pmp(OEt)$_2$-Val-Ala-Wang-resin.

The resin [Boc-D,L-CF$_2$Pmp(OEt)$_2$-Val-Ala-Wang-resin, 4.77 g] was treated with 95% trifluoroacetic acid (TFA)/5% H$_2$O (150 mL) for 2 hours. The resin was filtered, the solution concentrated under reduced pressure, resuspended in H$_2$O, and lyophilized to yield H-D,L-CF$_2$PmP(OEt)$_2$-Val-Ala-OH (1.184 g). The diastereomeric compounds were dissolved in methanol and separated by RP-HPLC on a Vydac 218TP1022 column (The Separations Group, Hesperia, Calif.) with a mobile phase of:

A: 0.1% TFA/H$_2$O

B: 0.1% TFA/acetonitrile; and a linear gradient of 0–50% B over 120 minutes.

The appropriate fractions were combined, concentrated under reduced pressure, and the earlier RP-HPLC peak was isolated (491 mg) which corresponded to H-CF$_2$Pmp-(OEt)$_2$-Val-Ala-OH (MS+1=522.3, Calculated=521.0).

A portion of H-CF$_2$Pmp(OEt)$_2$-Val-Ala-OH (250 mg) was dissolved in 100 mL of HOAc/H$_2$O (1:1) along with 50 molar equivalents of acetic anhydride at room temperature with stirring. After 30 minutes, an additional 200 equivalents of acetic anhydride was added. After 2 hours the solution was concentrated under reduced pressure, diluted with H$_2$O, and lyophilized. The crude peptide was dissolved in methanol and chromatographed by RP-HPLC on a Vydac 218TP1022 column with a mobile phase of:

A: 0.1% TFA/H$_2$O

B: 0.1% TFA/acetonitrile; and a linear gradient of 0% to 40% B over 120 minutes.

The appropriate fractions were combined, concentrated under reduced pressure and the major RP-HLPC peak was isolated (196 mg) which corresponded to Ac-CF$_2$Pmp-(OEt)$_2$-Val-Ala-OH.

Step B: Preparation of [1S-[1R*[R*(R*)]]]-[(4-{2-Acetylamino-2-[1-(1-dihexylcarbamoyl-ethylcarbamoyl)-2-methyl-propylcarbamoyl]-ethyl}-phenyl)-difluoro-methyl]-phosphoni acid diethyl ester [Ac-CF$_2$Pmp(OEt)$_2$-Val-Ala-N(C$_6$H$_{13}$)$_2$]

The title compound was prepared by starting with 97 mg of Ac-CF$_2$Pmp(OEt)$_2$-Val-Ala-OH which was treated with O-(7-azabenzotriazol-1-yl)-1,1,3,3-tetramethyl-uronium hexafluorophosphate (HATU, 127.8 mg, 2.0 eq.), 1-hydroxy-7-azabenzotriazole (HOAt, 45.7 mg, 2.0 eq.) and N,N-diisopropylethyl amine (DIEA, 117.1 µL, 4.0 eq.) in 20 mL of tetrahydrofuran (THF) at room temperature with stirring. After 5 minutes 78.4 µL (2.0 eq.) of dihexylamine was added. After the reaction was complete as monitored by RP-HPLC, the solution was concentrated under reduced pressure to an oil, partitioned between ethyl acetate and H$_2$O (100 mL each), and separated. The organic layer was washed with 5% aqueous citric acid (2×), 5% aqueous sodium bicarbonate (2×), brine (2×), concentrated under reduced pressure, and lyophilized (222 mg).

Step C: Preparation of [1S-[1R*[R*(R*)]]]-[(4-{2-Acetylamino-2-[1-(1-dihexylcarbamoyl-ethylcarbamoyl)-2-methyl-propylcarbamoyl]-ethyl}-phenyl)-difluoro-methyl]-phosphonic acid [Ac-CF$_2$Pmp-Val-Ala-N(C$_6$H$_{13}$)$_2$]

The title compound was prepared by starting with 97.2 mg of Ac-CF$_2$Pmp(OEt)$_2$-Val-Ala-N(C$_6$H$_{13}$)$_2$ which was treated with a solution of trimethylsilyl trifluoromethane-sulfonate (TMSOTf, 9.6 mL), TFA (33.0 mL), dimethyl sulfide (DMS, 7.4 mL), 1,2-ethanedithiol (EDT, 0.40 mL), and m-cresol (0.10 mL) at 0° C. with stirring. After 30 minutes, the solution was allowed to warm to room temperature for an additional 2 hours. The solution was then concentrated under reduced pressure and partitioned between ethyl ether and H$_2$O (100 mL each). The aqueous fraction was extracted with ethyl ether (2×), concentrated to an oil, dissolved in methanol, and chromatographed by RP-HPLC on a Vydac 218TP1022 column with a mobile phase of:

A: 0.1% TFA/H$_2$O

B: 0.1% TFA/acetonitrile; and a linear gradient of 20% to 80% B over 120 minutes.

The appropriate fractions were combined, concentrated under reduced pressure, and the major RP-HPLC peak was isolated (16.2 mg) which corresponded to Ac-CF$_2$Pmp-Val-Ala-N(C$_6$H$_{13}$)$_2$, (MS=674.6, Calculated=674.8).

Example 2

Step A: Preparation of [1S-[1R*[R*(R*)]]]-[(4-{2-Acetylamino-2-[1-(1-dipentylcarbamoyl-ethylcarbamoyl)-2-methyl-propylcarbamoyl]-ethyl}-phenyl)-difluoromethyl]-phosphonic acid [Ac-CF$_2$Pmp(OEt)$_2$-Val-Ala-N(C$_5$H$_{11}$)$_2$]

The title compound was prepared by starting with 97 mg of Ac-CF$_2$Pmp(OEt)$_2$-Val-Ala-OH which was treated with HATU (127.8 mg, 2.0 eq.), HOAt (45.7 mg, 2.0 eq.) and DIEA (117.1 µL, 4.0 eq.) in 20 mL of THF at room temperature with stirring. After 5 minutes, 78.4 µL (2.0 eq.) of dipentylamine was added. After the reaction was complete (RP-HPLC), the solution was concentrated under reduced pressure to an oil, partitioned between ethyl acetate and H$_2$O (100 mL each). The organic layer was washed with 5% aqueous citric acid (2×), 5% aqueous sodium bicarbonate (2×), brine (2×), concentrated under reduced pressure, and lyophilized (187 mg).

Step B: Preparation of [1S-[1R*[R*(R*)]]]-[(4-{2-Acetylamino-2-[1-(1-dipentylcarbamoyl-ethylcarbamoyl)-2-methyl-propylcarbamoyl]-ethyl}-phenyl)-difluoro-methyl]-phosphonic acid [Ac-CF$_2$Pmp-Val-Ala-N(C$_5$H$_{11}$)$_2$]

The title compound was prepared by starting with 97.2 mg of Ac-CF$_2$Pmp(OEt)$_2$-Val-Ala-N(C$_5$H$_{11}$)$_2$ which was treated with a solution of TMSOTf (9.6 mL), TFA (33.0 mL), DMS (7.4 mL), EDT (0.40 mL), and m-cresol (0.10 mL) at 0° C. with stirring. After 30 minutes the solution was allowed to warm to room temperature for an additional 2 hours. The solution was then concentrated under reduced pressure and partitioned between ethyl ether and H$_2$O (100 mL each). The aqueous fraction was extracted with ethyl ether (2×), concentrated to an oil, dissolved in methanol, and chromatographed by RP-HPLC on a Vydac 218TP1022 column with a mobile phase of:

A: 0.1% TFA/H$_2$O

B: 0.1% TFA/acetonitrile; and a linear gradient of 20% to 80% B over 120 minutes.

The appropriate fractions were combined, concentrated under reduced pressure and the major RP-HPLC peak was isolated (41.6 mg) which corresponded to Ac-CF$_2$Pmp-Val-Ala-N(C$_5$H$_{11}$)$_2$, (MS=645.4, Calculated=646.7).

Example 3

Preparation of [1S-[1R*[R*(R*)]]]-[(4-{2-Acetylamino-2-[1-(1-dioctylcarbamoyl-ethylcarbamoyl)-2-methyl-propylcarbamoyl]-ethyl}-phenyl)-difluoro-methyl]-phosphonic acid (Ac-CF$_2$Pmp-Val-Ala-N(C$_8$H$_{17}$)$_2$], (MS=730.5, Calculated=730.9). The title compound was prepared as above.

Example 4

Step A: Preparation of [1S-[1R*[R*(R*)]]]-2-{2-[2-Acetylamino-3-(4-benzyloxy-phenyl)-propionylamino]-3-methyl-butyrylamino}-propionic acid [Ac-Tyr(Bzl)-Val-Ala-OH]

Starting with 5.75 g of Sasrin® resin (2-methoxy-4-alkoxybenzyl alcohol resin, 0.87 meq, 5.00 mmol), the resin was washed with DCM (3×) and DMF (3×). Fmoc-Ala-OH (6.22 g, 4.0 eq.) was coupled to the resin in the presence of DCC (1.67 g, 2.0 eq.) and 4-dimethylaminopyridine (DMAP, 0.061 g, 0.1 eq.) in DMF and the Fmoc protecting group was removed by two treatments with 20% piperidine in DMF. Fmoc-Val-OH (6.78 g, 4.0 eq.) and Fmoc-Tyr(Bzl)-OH (9.87 g, 4.0 eq.) were coupled in the presence of DCC (2.70 g, 4.0 eq.) and HOBt (4.12 g, 4.0 eq.) in NMP and the Fmoc amino protecting group was removed, as above. After the reaction was complete, as judged by the Kaiser ninhydrin test, the resin was washed with NMP (3×), DCM (3×). The resin was acetylated with 50% acetic anhydride in DCM (2×), washed with DCM (3×), and dried under reduced pressure to yield Ac-Tyr(Bzl)-Val-Ala-Sasrin® resin.

The peptide-Sasrin® resin was treated with 2% TFA in DCM (2×150 mL) for 15 minutes. The resin was filtered, concentrated under reduced pressure, triturated with ethyl ether, solubilized in water/acetonitrile, and lyophilized to yield Ac-Tyr(Bzl)-Val-Ala-OH (1.55 g). The peptide was purified by preparative RP-HPLC on a Vydac 218TP101550 column with a mobile phase as follows:

A: 0.1% TFA/$H_2O$

B: 0.1% TFA/acetonitrile with a linear gradient of 15% to 45% B over 120 minutes.

The appropriate fractions were combined, concentrated under reduced pressure, and lyophilized (470 mg) to yield Ac-Tyr(Bzl)-Val-Ala-OH, (MS=482.6, Calculated=483.57).

Step B: Preparation of [1S-[1R*[R*(R*)]]]-2-[2-Acetylamino-3-(4-benzyloxy-phenyl)-propionylamino]-N-(1-dihexyl-carbamoyl-ethyl)-3-methyl-butyramide [Ac-Tyr(Bzl)-Val-Ala-N($C_6H_{13}$)$_2$]

The title compound was prepared by starting with 80.7 mg of Ac-Tyr(Bzl)-Val-Ala-OH which was treated with HATU (126.9 mg, 2.0 eq.), HOAt (45.4 mg, 2.0 eq.), and DIEA (110.7 mL, 4.0 eq.) in 50 mL of THF at room temperature while stirring. After 5 minutes, 77.8 mL (2.0 eq.) of dihexylamine was added. After the reaction was complete as monitored by RP-HPLC, the solution was concentrated under reduced pressure yielding an oil, which was partitioned between ethyl acetate and water (150 mL) and separated. The organic layer was washed with 5% aqueous citric acid (2×), 5% aqueous sodium bicarbonate (2×), brine (2×), concentrated under reduced pressure, and lyophilized (200 mg).

Step C: Preparation of [1S-[1R*[R*(R*)]]]-Phosphoric acid mono-(4-{2-acetylamino-2-[1-(1-dihexylcarbamoyl-ethylcarbamoyl)-2-methyl-propylcarbamoyl]-ethyl}-phenyl) ester [Ac-Tyr(PO$_3$H$_2$)-Val-Ala-N($C_6H_{13}$)$_2$]

The title compound was prepared by starting with 200 mg of Ac-Tyr(Bzl)-Val-Ala-N($C_6H_{13}$)$_2$ which was reduced with hydrogen under high pressure with 20% Pd/C catalyst in methanol. The catalyst was filtered. The solution was concentrated under reduced pressure, dissolved, and lyophilized (15B mg). The peptide was phosphotitylated with 1H-tetrazole (79.0 mg, 4.0 eq.) and di-t-butyl diethylphosphoramidite (312 mL, 4.0 eq.) in DCM (50 mL) while stirring at room temperature for 1 hour. The compound was then treated with 2.0 mL 70% aqueous t-butyl-hydroperoxide to the solution for 1 hour. The solution was then concentrated under reduced pressure. The peptide was deprotected with 95% TFA/5% water (20 mL) while stirring for 1 hour. The solution was then concentrated under reduced pressure and purified by preparative RP-HPLC using a gradient of 20% to 50% B over 120 minutes. The appropriate fractions were combined and lyophilized yielding Ac-Tyr(PO$_3$H$_2$)-Val-Ala-N($C_6H_{13}$)$_2$ (11.0 mg, MS=639.3, Calculated=640.43).

Example 5

Preparation of [S-[R*[R*(S*)]]]-Phosphoric acid mono-(4-{2-acetylamino-2-[1-(1-dihexylcarbamoyl-ethyl carbamoyl)-2-methyl-propylcarbamoyl]-ethyl}-phenyl) ester [Ac-Tyr(PO$_3$H$_2$)-Val-DAla-N($C_6H_{13}$)$_2$], (MS=639.6, 12, Calculated=640.4). The title compound was prepared as above.

Example 6

Preparation of [1S-[1R*[R*(R*)]]]-Phosphoric acid mono-(4-{2-acetylamino-2-[1-(1-dibutylcarbamoyl-ethyl-carbamoyl)-2-methyl-propylcarbamoyl]-ethyl}-phenyl) ester [Ac-Tyr(PO$_3$H$_2$)-Val-Ala-N($C_4H_9$)$_2$], (MS=583.6, Calculated=584.4). The title compound was prepared as above.

Example 7

Preparation of [1R-[1R*[S*(S*)]]]-Phosphoric acid mono-(4-{2-acetylamino-2-[1-(1-dibutylcarbamoyl-ethyl-carbamoyl)-2-methyl-propylcarbamoyl]-ethyl}-phenyl) ester [Ac-Tyr(PO$_3$H$_2$)-Val-DAla-N($C_4H_9$)$_2$], (MS=583.6, Calculated=584.4). The title compound was prepared as above.

Example 8

Preparation of [1S-[1R*[R*(R*)]]]-Phosphoric acid mono-(4-{2-acetylamino-2-[1-(1-dipentylcarbamoyl-ethyl-carbamoyl)-2-methyl-propylcarbamoyl]-ethyl}-phenyl) ester [Ac-Tyr(PO$_3$H$_2$)-Val-Ala-N($C_5H_{11}$)$_2$], (MS=611.6, Calculated=612.4). The title compound was prepared as above.

Example 9

Preparation of [1R-[1R*[S*(S*)]]]-Phosphoric acid mono-(4-{2-acetylamino-2-[1-(1-dipentylcarbamoyl-ethyl-carbamoyl)-2-methyl-propylcarbamoyl]-ethyl}-phenyl) ester [Ac-Tyr(PO$_3$H$_2$)-Val-DAla-N($C_5H_{11}$)$_2$], (MS=611.5, Calculated=612.4). The title compound was prepared as above.

Example 10

Preparation of [1S-[1R*[R*(R*)]]]-Phosphoric acid mono-(4-{2-acetylamino-2-[1-(1-dioctylcarbamoyl-ethylcarbamoyl)-2-methyl-propylcarbamoyl]-ethyl}-phenyl) ester [Ac-Tyr(PO$_3$H$_2$)-Val-Ala-N($C_8H_{17}$)$_2$], (MS=696.4, Calculated=696.9). The title compound was prepared as above.

Example 11

[S-[R*[R*(S*)]]]-Phosphoric acid mono-(4-{2-acetyl-amino-2-[1-(1-dioctylcarbamoyl-ethylcarbamoyl)-2-methyl-propylcarbamoyl]-ethyl}-phenyl) ester [Ac-Tyr(PO$_3$H$_2$)-Val-DAla-N($C_8H_{17}$)$_2$], (MS=696.4, Calculated=696.9). The title compound was prepared as above.

Example 12

Step A: Preparation of [S-(R*,R*)]-2-{2-[3-(4-Benzyloxy-phenyl)-propionylamino]-3-methyl-butyrylamino}-propionic acid [Ppa(Bzl)-Val-Ala-OH]

Starting with 5.75 g of Sasrin® resin (0.87 meq, 5.00 mmol), the resin was washed with DCM (3×) and DMF (3×).

Fmoc-Ala-OH (6.22 g, 4.0 eq.) was coupled to the resin in the presence of DCC (1.67 g, 2.0 eq.) and DMAP (0.061 g, 0.1 eq.) in DMF and the Fmoc protecting group was removed by two treatments with 20% piperidine in DMF. Fmoc-Val-OH (6.78 g, 4.0 eq.) and 3-[4-(benzyl ether)-phenyl]propionic acid [Ppa(Bzl)-OH, 5.12 g, 4.0 eq.] were coupled in the presence of DCC (2.70 g, 4.0 eq.) and HOBt (4.12 g, 4.0 eq.) in NMP and the Fmoc amino protecting group was removed, as above. After the reaction was complete, as judged by the Kaiser ninhydrin test, the resin was washed with NMP (3×), DCM (3×) and dried under reduced pressure to yield Ppa(Bzl)-Val-Ala-Sasrin® resin.

The peptide-Sasrin® resin was treated with 2% TFA in DCM (2×150 mL) for 15 minutes. The resin was filtered, concentrated under reduced pressure, triturated with ethyl ether, solubilized in water/acetonitrile, and lyophilized to yield Ppa(Bzl)-Val-Ala-OH (1.24 g). The peptide was purified by preparative RP-HPLC on a Vydac 218TP101550 column with a mobile phase as follows:

A: 0.1% TFA/$H_2O$

B: 0.1% TFA/acetonitrile with a linear gradient of 15% to 45% B over 120 minutes.

The appropriate fractions were combined, concentrated under reduced pressure, and lyophilized to yield Ppa(Bzl)-Val-Ala-OH (376 mg).

Step B: Preparation of [S-(R*,R*)]-2-[3-(4-Benzyloxy-phenyl)-propionylamino]-N-(1-(1-dihexylcarbamoyl)-ethyl)-3-methyl-butyramide [Ppa(Bzl)-Val-Ala-N($C_6H_{13}$)$_2$]

The title compound was prepared by starting with 86.2 mg of Ppa(Bzl)-Val-Ala-OH which was treated with HATU (253.8 mg, 2.0 eq.), HOAt (90.8 mg, 2.0 eq.) and DIEA (221.4 mL, 4.0 eq.) in 50 mL of THF at room temperature while stirring. After 5 minutes, 155.6 mL (2.0 eq.) of dihexylamine was added. After the reaction was completed as monitored by RP-HPLC, the solution was concentrated under reduced pressure yielding an oil, partitioned between ethyl acetate and water (150 mL), and separated. The organic layer was washed with 5% aqueous citric acid (2×), 5% aqueous sodium bicarbonate (2×), brine (2×), concentrated under reduced pressure, and lyophilized (120 mg).

Step C: Preparation of [S-(R*,R*)]-Phosphoric acid mono-(4-{2-[1-(1-(dihexylcarbamoyl)-ethylcarbamoyl)-2-methyl-propylcarbamoyl]-ethyl}-phenyl) ester [Ppa($PO_3H_2$)-Val-Ala-N($C_6H_{13}$)$_2$]

The title compound was prepared by starting with 115 mg of Ppa(Bzl)-Val-Ala-N($C_6H_{13}$)$_2$ which was reduced with hydrogen under high pressure with 20% Pd/C catalyst in methanol. The catalyst was filtered. The solution was concentrated under reduced pressure, dissolved, and lyophilized. The peptide (110 mg) was phosphotitylated with 1H-tetrazole (65.0 mg, 4.0 eq.) and di-t-butyl diethylphosphoramidite (256.4 mL, 4.0 eq.) in DCM (50 mL) while stirring at room temperature for 1 hour. The compound was then treated with 2.0 mL 70% aqueous t-butylhydroperoxide to the solution for 1 hour. The solution was then concentrated under reduced pressure. The peptide was deprotected with 95% TFA/5% water (20 mL, 60 minutes). The solution was concentrated under reduced pressure and purified by preparative RP-HPLC using a gradient of 20% to 50% B over 120 minutes. The appropriate fractions were combined and lyophilized yielding Ppa($PO_3H_2$)-Val-Ala-N($C_6H_{13}$)$_2$ (10.4 mg).

Biological Methods

Expression and Purification of the p85 PI3-Kinase SH2 Domain Fusion Protein.

The pGEX plasmid expressing the carboxy-terminal SH2 of the p85 subunit of PI3-kinase in a glutathione-s-transferase (GST) fusion protein was used in these studies. Expression and purification of the fusion protein was performed as previously described by Zhu, et al., *J. Biol. Chem.*, 1993;268:1175. To prepare [$^{35}$S]p85 fusion proteins, a 125 mL overnight culture of *E. coli* expressing the p85-GST fusion protein was added to 1000 mL of LB broth containing 100 μg/mL ampicillin. The cultures were incubated at 37° C. until reaching a density of $A_{600}$=1.0. 1 mM of isopropyl-β-D-thiogalactoside was added and 15 minutes later, 10 mCi of trans $^{35}$S-label was added and cultures incubated for an additional 3 hours at 37° C. The cells were then lysed by sonication and fusion proteins purified over glutathione-agarose beads.

Preparation of PDGF-β Receptor Tyrosine Kinase Intracellular Domain.

Lysates from SF9 insect cells expressing the PDGF-β receptor tyrosine kinase intracellular domain, obtained from L. T. Williams at the University of California at San Francisco, were incubated with M2 affinity beads and the complexes were washed several times with Tris buffer containing protease inhibitors and sodium orthovanadate. Complexes were centrifuged and resuspended in N-[2-hydroxyethyl]piperazine-N'-[2-ethane sulfonic acid] (HEPES) buffer containing 1 mM adenosine triphosphate (ATP), 10 mM $MnCl_2$, and 5 mM $MgCl_2$ to stimulate phosphorylation of the PDGF receptor.

p85 SH2—PDGF-β Receptor Binding Assay

Binding of [$^{35}$S]p85 SH2 fusion proteins to the phosphorylated PDGF-β receptor tyrosine kinase intracellular domain was assayed in Hepes buffer containing ethylene diamine tetraacetic acid (EDTA), NP-40 and 10 mg/mL of each of the protease inhibitors, PMSF, pepstatin, leupeptin, and aprotinin. Binding assays were performed in 96-well millipore filter plates in a final volume of 250 μL of HEPES buffer containing 135 μL phosphorylated PDGF receptor-beads complex (1 μg receptor/well), 10 μL [$^{35}$S]p85 SH2 fusion protein (30,000 cpm/well), and 5 μL of peptide inhibitor as indicated. Samples were incubated at 25° C. for 20 minutes with continuous rocking. Binding was terminated by filtration through the filter plates using a millipore multiscreen filtration manifold Millipore, Bedford, Mass.). Filter plates were washed four times with 0.15 mL Hepes buffer followed by the addition of 40 μL hi-load scintillant and radioactivity retained on the filters was counted in a Wallac 1450 Microbeta counter (Wallac Inc, Gaithersburg, Md.). Total binding was defined as [$^{35}$S]p85 fusion protein bound to the PDGF-β receptor-bead complex retained on the filter plate after washing. Nonspecific binding was defined as radioactivity retained on the filter plates in the presence of excess unlabeled p85 fusion protein. Specific binding was defined as total binding minus nonspecific binding. $IC_{50}$ values were calculated by weighted nonlinear regression curve fitting.

Cell Culture

Smooth muscle cells were isolated from the thoracic aorta of rats (RASMC) and explanted according to the method of Ross, *J. Biol. Chem.*, 1971;30:172–86. Cells were grown in Dulbecco's modified Eagle's medium (DMEM, Gibco) containing 10% fetal calf serum (FBS, Hyclone, Logan, Utah), 1% glutamine (Gibco) and 1% penicillin/streptomycin (Gibco). Cells were identified as smooth muscle cells by their "hill and valley" growth pattern and by fluorescent staining with a monoclonal antibody specific for SMC μ-actin (Sigma). RASMC were used between passages 5 and 20 for all experiments. Test compounds were prepared in dimethylsulfoxide (DMSO) in order to achieve consistency in the vehicle and to ensure compound solubility. Appropriate DMSO controls were simultaneously evaluated with the test compounds.

PDGF Receptor/PI 3-Kinase Cell Association Assay

Rat aortic smooth muscle cells were grown to confluency in 100 mm dishes. Growth medium was removed and replaced with serum-free medium and cells were incubated at 37° C. for an additional 24 hours. Test compounds were then added directly to the medium and cells incubated for an additional 24 hours. After 24 hours PDGF-BB was added at a final concentration of 30 ng/mL for 5 minutes at 37° C. to stimulated autophosphorylation of the PDGF receptor and association of PI 3-kinase to the phosphorylated receptors. Following growth factor treatment, the media was removed, and cells were washed with cold phosphate-buffered saline and immediately lysed with 1 mL of lysis buffer (50 mM HEPES ([pH 7.5], 150 mM NaCl, 10% glycerol, 1% Triton-X 100, 1 mM ethylene glycol-bis(β-aminoethyl ether) N, N, N', N'-tetraacetic acid (EGTA), 50 mM NaF, 1 mM sodium orthovanadate, 30 mM p-nitrophenyl phosphate, 10 mM sodium pyrophosphate, 1 mM phenylmethyl sulfonyl fluoride, 10 μg/mL aprotinin and 10 μg/mL leupeptin). Lysates were centrifuged at 10,000×g for 10 minutes. Supernatants were incubated for 2 hours with 10 μL of antihuman PDGF receptor polyclonal antibody (1:1000) which recognizes the PDGF receptor α and β isoforms. Following the incubation, protein-A-sepharose beads were added for 2 hours with continuous mixing and immune complexes bound to the beads washed 4 times with 1 mL lysis wash buffer. Immune complexes were solubilized in 30 μL of Laemmli sample buffer and electrophoresed in 4% to 20% SDS polyacrylamide gels. Following electrophoresis, separated proteins were transferred to nitrocellulose and immunoblotted with antirat PI 3-kinase antiserum which recognizes the 85 kDa subunit of PI 3-kinase. Following incubation with $^{125}$I-protein-A, p85 protein levels were detected by phosphorimage analysis and protein bands quantitated via densitometry. $IC_{50}$ values were generated from the densitometric data.

TABLE 1

Inhibition of PDGF Receptor/PI3-Kinase Association

| Example No. | Binding $IC_{50}$ | Cellular $IC_{50}$ |
|---|---|---|
| 6 | 1.6 ± 0.32 μM (n = 7) | 37.5 μM |
| 8 | 0.22 μM (n = 2) | |
| 2 | 0.29 ± 0.08 μM (n = 4) | 30% @ 25 μM |
| 4 | 0.08 ± 0.01 μM (n = 3) | 27% @ 25 μM |
| 1 | 0.45 ± 0.04 μM (n = 4) | — |
| 10 | 3.5 ± 0.5 μM (n = 4) | — |
| 3 | 12.2 ± 0.9 μM (n = 4) | — |

What is claimed is:

1. A compound of the Formula III

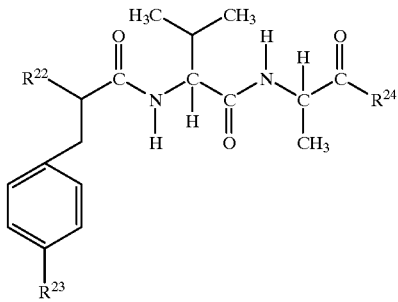

wherein
R$^{22}$ is hydrogen, —NR$^a$R$^b$, —NR$^e$COR$^f$, —NR$^k$CO$_2$CH$_2$-phenyl, or —NR$^j$CO$_2$-fluorenylmethyl;
R$^{23}$ is —CY$^1$Y$^2$PO$_3$R$^{18}$R$^{19}$ or —OPO$_3$R$^{20}$R$^{21}$;
R$^{24}$ is —NR$^{14}$R$^{15}$;
R$^a$ R$^b$, R$^e$, R$^j$, R$^k$, R$^{18}$ R$^{19}$, R$^{20}$, and R$^{21}$ are independently hydrogen or C$_1$–C$_6$ alkyl;
R$^f$ is C$_1$–C$_6$ alkyl;
R$^{14}$ and R$^{15}$ are independently hydrogen, C$_1$–C$_8$ alkyl, C$_2$–C$_5$ alkenyl, C$_2$–C$_5$ alkynyl, or C$_3$–C$_7$ cycloalkyl; and
Y$^1$ and Y$^2$ are independently hydrogen or halogen, and the pharmaceutically acceptable salts, esters, amides, and prodrugs thereof.

2. The compound of claim 1 wherein R$^{22}$ is —NR$^e$COR$^f$.

3. The compound of claim 1 wherein R$^{25}$ is 2-propyl, and R$^{26}$ is methyl.

4. The compound of claim 2 wherein —NR$^e$COR$^f$ is —NHCOCH$_3$.

5. The compound of claim 1 wherein R$^{23}$ is —CF$_2$PO$_3$H$_2$ or —OPO$_3$H$_2$.

6. The compound of claim 1 wherein R$^{22}$ is —NR$^e$COR$^f$, R$^{23}$ is —CF$_2$PO$_3$H$_2$ or —OPO$_3$H$_2$, and R$^{24}$ is —NR$^{14}$R$^{15}$.

7. A method of treating cancer that comprises administering to a patient having cancer a therapeutically effective amount of a compound of claim 1.

8. A method of treating or preventing restenosis that comprises administering to a patient having restenosis or at risk of having restenosis a therapeutically effective amount of a compound of claim 1.

9. A method of treating arthritis that comprises administering to a patient having arthritis a therapeutically effective amount of a compound of claim 1.

10. A method of treating dermatitis that comprises administering to a patient having dermatitis a therapeutically effective amount of a compound of claim 1.

11. A method of treating atherosclerosis that comprises administering to a patient having atherosclerosis a therapeutically effective amount of a compound of claim 1.

12. A method of treating vein graft intimal hyperplasia that comprises administering to a patient having vein graft intimal hyperplasia a therapeutically effective amount of a compound of claim 1.

13. A method of treating neointimal hyperplasia of vascular smooth muscle that comprises administering to a patient having neointimal hyperplasia of vascular smooth muscle a therapeutically effective amount of a compound of claim 1.

14. A method of treating psoriasis that comprises administering to a patient having psoriasis a therapeutically effective amount of a compound of claim 1.

15. A pharmaceutically acceptable composition that comprises a compound of claim 1.

16. A compound selected from:

[1S-[1R*[R*(R*)]]]-2-[2-(2-Acetylamino-3-{4-[(diethoxy-phosphoryl)-difluoro-methyl]-phenyl}-propionylamino)-3-methyl-butyrylamino]-propionic acid;

[1S-[1R*[R*(R*)]]]-[(4-{2-Acetylamino-2-[1-(1-dihexylcarbamoyl-ethylcarbamoyl)-2-methyl-propylcarbamoyl]-ethyl}-phenyl)-difluoro-methyl]-phosphonic acid diethyl ester;

[1S-[1R*[R*(R*)]]]-[(4-{2-Acetylamino-2-[1-(1-dihexylcarbamoyl-ethylcarbamoyl)-2-methyl-propylcarbamoyl]-ethyl}-phenyl)-difluoro-methyl]-phosphonic acid;

[1S-[1R*[R*(R*)]]]-[(4-{2-Acetylamino-2-[1-(1-dipentylcarbamoyl-ethylcarbamoyl)-2-methyl-propylcarbamoyl]-ethyl}-phenyl)-difluoro-methyl]-phosphonic acid;

[1S-[1R*[R*(R*)]]]-[(4-{2-Acetylamino-2-[1-(1-dipentylcarbamoyl-ethylcarbamoyl)-2-methyl-propylcarbamoyl]-ethyl}-phenyl)-difluoro-methyl]-phosphonic acid;

[1S-[1R*[R*(R*)]]]-[(4-{2-Acetylamino-2-[1-(1-dioctylcarbamoyl-ethylcarbamoyl)-2-methyl-propylcarbamoyl]-ethyl}-phenyl)-difluoro-methyl]-phosphonic acid;

[1S-[1R*[R*(R*)]]]-Phosphoric acid mono-(4-{2-acetylamino-2-[1-(1-dibutylcarbamoyl-ethylcarbamoyl)-2-methyl-propylcarbamoyl]-ethyl}-phenyl) ester;

[1R-[1R*[S*(S*)]]]-Phosphoric acid mono-(4-{2-acetylamino-2-[1-(1-dibutylcarbamoyl-ethylcarbamoyl)-2-methyl-propylcarbamoyl]-ethyl}-phenyl) ester;

[1S-[1R*[R*(R*))]]]-Phosphoric acid mono-(4-{2-acetylamino-2-[1-(1-dipentylcarbamoyl-ethylcarbamoyl)-2-methyl-propylcarbamoyl]-ethyl}-phenyl) ester;

[1R-[1R*[S*(S*)]]]-Phosphoric acid mono-(4-{2-acetylamino-2-[1-(1-dipentylcarbamoyl-ethylcarbamoyl)-2-methyl-propylcarbamoyl]-ethyl}-phenyl) ester;

[1S-[1R*[R*(R*)]]]-Phosphoric acid mono-(4-{2-acetylamino-2-[1-(1-dihexylcarbamoyl-ethylcarbamoyl)-2-methyl-propylcarbamoyl]-ethyl}-phenyl) ester;

[1S-[1R*[R*(S*)]]]-Phosphoric acid mono-(4-{2-acetylamino-2-[1-(1-dihexylcarbamoyl-ethylcarbamoyl)-2-methyl-propylcarbamoyl]-ethyl}-phenyl) ester;

[1S-[1R*[R*(S*)]]]-Phosphoric acid mono-(4-{2-acetylamino-2-[1-(1-dioctylcarbamoyl-ethylcarbamoyl)-2-methyl-propylcarbamoyl]-ethyl}-phenyl) ester;

[1S-[1R*[R*(R*)]]]-2-{2-[2-Acetylamino-3-(4-benzyloxy-phenyl)-propionylamino]-3-methyl-butyrylamino}-propionic acid;

[1S-[1R*[R*(R*)]]]-2-[2-Acetylamino-3-(4-benzyloxy-phenyl)-propionylamino]-N-(1-dihexylcarbamoyl-ethyl)-3-methyl-butyramide;

[1S-[1R*[R*(R*)]]]-Phosphoric acid mono-(4-{2-acetylamino-2-[1-(1-dihexylcarbamoyl-ethylcarbamoyl)-2-methyl-propylcarbamoyl]-ethyl}-phenyl) ester;

[1S-[1R*[R*)]]]-2-{2-[3-(4-Benzyloxy-phenyl)-propionylamino]-3-methyl-butyrylamino}-propionic acid;

[1S-[1R*[R*)]]]-2-[3-(4-Benzyloxy-phenyl)-propionylamino]-N-(1-dihexylcarbamoyl)-ethyl)-3-methyl-butylamide; and

[1S-[1R*[R*)]]]-Phosphoric acid mono-(4-{2-[1-(1-dihexylcarbamoyl-ethylcarbamoyl)-2-methyl-propylcarbamoyl]-ethyl}-phenyl) ester.

* * * * *